(12) United States Patent
Helal et al.

(10) Patent No.: US 8,012,969 B2
(45) Date of Patent: Sep. 6, 2011

(54) 11C-LABELED BENZYL-LACTAM COMPOUNDS AND THEIR USE AS IMAGING AGENTS

(75) Inventors: Christopher John Helal, East Lyme, CT (US); Gunnar Antoni, Uppsala (SE); Bengt Langstrom, Uppsala (SE); Jia Zhi Sheng, Uppsala (SE); Susan Beth Sobolov-Jaynes, Essex, CT (US); Timothy James McCarthy, Mystic, CT (US)

(73) Assignee: GE Healthcare Limited, Buckinghamshire (GB)

( * ) Notice: Subject to any disclaimer, the term of this patent is extended or adjusted under 35 U.S.C. 154(b) by 813 days.

(21) Appl. No.: 11/813,779

(22) PCT Filed: Jan. 11, 2006

(86) PCT No.: PCT/IB2006/000028
§ 371 (c)(1),
(2), (4) Date: Dec. 12, 2007

(87) PCT Pub. No.: WO2006/075226
PCT Pub. Date: Jul. 20, 2006

(65) Prior Publication Data
US 2008/0206137 A1  Aug. 28, 2008

Related U.S. Application Data

(60) Provisional application No. 60/643,453, filed on Jan. 13, 2005.

(51) Int. Cl.
*A61K 31/535* (2006.01)
*A61K 31/497* (2006.01)
*C07D 245/02* (2006.01)
*C07D 413/14* (2006.01)
*C07D 401/14* (2006.01)
*C07D 403/14* (2006.01)
*C07D 405/14* (2006.01)

(52) U.S. Cl. ........... 514/235.5; 514/254.01; 514/253.09; 514/253.11; 540/470; 540/575; 544/121; 544/364; 546/194; 546/208; 546/278.4

(58) Field of Classification Search ................. 544/372, 544/374, 121, 364; 514/235.5, 254.01, 253.09, 514/253.11, 253.5; 540/470, 575; 546/194, 546/208, 278.4
See application file for complete search history.

(56) References Cited

U.S. PATENT DOCUMENTS
2003/0083337 A1   5/2003  Howard et al.
2005/0245521 A1*  11/2005 Brodney et al. ............ 514/235.5

FOREIGN PATENT DOCUMENTS
WO   97/36867    10/1997
WO   2005/090300  9/2005

OTHER PUBLICATIONS

Verhaar et al., Technetium-99m Radiolabeling Using a Phage-Derived Single-Chain Fv With a C-Terminal Cysteine, Journal of Nuclear Medicine, vol. 37, No. 5, May 1996.*
PCT/IB2006/000028 ISR/WO dated Apr. 2006.
PCT/IB2006/000028 IPRP Dated Dec. 2006.
Luurtsema, G., et.al. "Transport across the blood-brain barrier: stereoselectivity and PET-tracers" Molecular Imaging and Biology, Elsevier, vol. 6, No. 5, Sep. 2004, pp. 306-318.

* cited by examiner

*Primary Examiner* — James O. Wilson
*Assistant Examiner* — Ebenezer O Sackey

(57) ABSTRACT

The invention relates to $^{11}$C-labeled compounds, their preparation, compositions comprising an effective amount of a $^{11}$C-labeled compound, and the use of a $^{11}$C-labeled compound as a radiopharmaceutical for positron emission tomography.

15 Claims, No Drawings

11C-LABELED BENZYL-LACTAM COMPOUNDS AND THEIR USE AS IMAGING AGENTS

This application is a filing under 35 U.S.C. 371 of international application number PCT/IB2006/000028, filed Jan. 11, 2006, which claims priority to application number 60/643,453 filed Jan. 13, 2005, in the United States the entire disclosure of which is hereby incorporated by reference.

FIELD OF THE INVENTION

This invention relates to $^{11}$C-labeled compounds, their preparation, and their use as radiopharmaceuticals for positron emission tomography ("PET").

BACKGROUND OF THE INVENTION

Serotonin plays a role in several psychiatric disorders, including anxiety, Alzheimer's disease, depression, nausea and vomiting, sleep, pain, eating disorders, and migraine headache. Serotonin also plays a role in both the positive and negative symptoms of schizophrenia. The central nervous system ("CNS") distribution of serotonin and one of its receptors, the serotonin type 1B ("5HT$_{1B}$") receptor, coupled with the functional effects of serotonin suggest that 5HT$_{1B}$ receptor antagonists can exert important neurological and behavioral effects. In addition, 5HT$_{1B}$ antagonists have been shown to have antidepressant properties. Agents that selectively inhibit the 5HT$_{1B}$ receptor, therefore, represent a useful approach to the treatment of psychiatric disorders including major depressive disorder.

A difficulty in the development of compounds useful for the treatment of psychiatric disorders has been the lack of appropriate animal models, the limited accessibility to the brain for pharmacokinetic measurements and lack of adequate direct biomarkers relating to action on the target system. Therefore, more accurate models for performing pharmacokinetic ("PK") and pharmacodynamic ("PD") modeling would be achievable if central pharmacokinetic parameters such as receptor occupancy are used instead of plasma exposures.

PET is a non-invasive imaging technique that has been widely used in neuropsychopharmacological drug development. In particular, measuring the degree of receptor occupancy in the brain has been used to guide dose-selection for antidepressant and antipsychotic drugs. Additionally, PET can be used to determine the appropriate dosing regimen for a centrally acting agent by determining the rate of onset, magnitude and duration of CNS target interaction versus the plasma half-life. See, e.g., Andree B, Nyberg S, Ito H, Ginovart N, Brunner F, Jaquet F, Halldin C and Farde L. Positron emission tomographic analysis of dose-dependent MDL 100,907 binding to 5-hydroxytryptamine-2A receptors in the human brain. *Journal of Clinical Psychopharmacology* 18: 317-323, 1998. PET is based on the external detection and recording of the decay of positron emitters incorporated in compounds administered to in a subject. For example, molecules of biological interest (water, sugars, amino acids or synthetic compounds) have been labeled with short-lived positron emitter isotopes of biological nuclei (e.g., $^{11}$C), providing radiotracers having high specific activity and preserved biochemical properties.

Recently developed PET instruments allow one to obtain time-varying three-dimensional maps of the absolute radioactivity concentration distribution following compound administration. By applying tracer-kinetic modeling to these PET regional time activity curves ("TACs"), it is possible to estimate absolute values of the physiological parameters that determine the interactions and fate of the radiotracer compound. PET can be used for assessing in vivo the transport and binding regional parameters of a given drug in the tissue of a mammal, or for investigating the regional effects of a drug on physiological parameters, such as blood flow, energy metabolism, or protein synthesis rate.

The utility of radioactive agents with affinity for receptors, such as serotonin receptors, for imaging tissue, either directly or indirectly, is known. For example, C.-Y. Shiue et al., *Synapse*, 1997, 25, 147 and S. Houle et al., *Can. Nucl. Med. Commun.*, 1997, 18, 1130, describe the use of 5HT$_{1A}$ receptor ligands to image 5HT$_{1A}$ receptors in the human brain using PET. See also C. Halldin et al., *Curr. Pharm. Design*, 2001, 7(18) 1907-29.

There is a great need for CNS ligands, including 5HT$_{1B}$ ligands, that can be labeled with PET radionuclide and used for imaging tissue expression of this receptor system.

SUMMARY OF THE INVENTION

The present invention relates to compounds of the formula I:

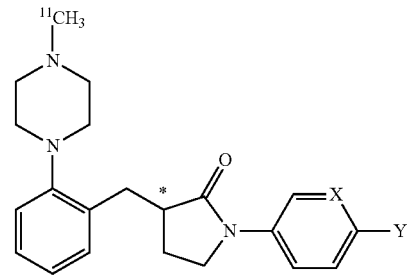

Formula I and pharmaceutically acceptable salts thereof, wherein X is CH or N;

Y is —C(OR$^1$)(R$^2$)$_2$ or —N(R$^3$)$_2$;

R$^1$ is H or C$_1$-C$_6$ alkyl;

each R$^2$ is independently C$_1$-C$_6$ alkyl, or both R$^2$ groups are taken together to form —(CH$_2$)$_n$—, where n is an integer ranging from 2 to 7;

each R$^3$ is independently C$_1$-C$_6$ alkyl, or both R$^3$ groups are taken together to form —(CH$_2$)$_2$—O—(CH$_2$)$_2$—, —(CH$_2$)$_2$—(NR$^4$)—(CH$_2$)$_2$— or —(CH$_2$)$_m$—, where m is an integer ranging from 2 to 7;

R$^4$ is H or CH$_3$; and

\* is a chiral carbon atom, wherein said carbon is a racemate, an (R)-enantiomer, an (S)-enantiomer, or a mixture thereof.

A compound of Formula I or a pharmaceutically acceptable salt thereof (each being a "$^{11}$C-labeled compound") is useful for radiopharmaceuticals for positron emission tomography in a mammal. Herein a $^{11}$C-labeled compound of Formula I or a pharmaceutically acceptable salt thereof is also referred to as a $^{11}$C-labeled compound; the descriptions are used interchangeably.

The invention also relates to compositions comprising an effective amount of a $^{11}$C-labeled compound and a physiologically acceptable carrier or vehicle.

The invention further relates to compounds of formula II:

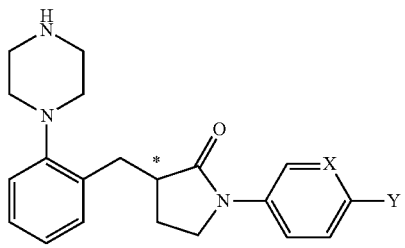

Formula II wherein X is CH or N;
Y is —C(OR$^1$)(R$^2$)$_2$ or —N(R$^3$)$_2$;
R$^1$ is H or C$_1$-C$_6$ alkyl;
each R$^2$ is independently C$_1$-C$_6$ alkyl, or both R$^2$ groups are taken together to form —(CH$_2$)$_n$—, where n is an integer ranging from 2 to 7;
each R$^3$ is independently C$_1$-C$_6$ alkyl, or both R$^3$ groups are taken together to form —(CH$_2$)$_2$—O—(CH$_2$)$_2$—, —(CH$_2$)$_2$—(NR$^4$)—(CH$_2$)$_2$— or —(CH$_2$)$_m$—, where m is an integer ranging from 2 to 7;
R$^4$ is H or CH$_3$; and
* is a chiral carbon atom, wherein said carbon is a racemate, an (R)-enantiomer, an (S)-enantiomer, or a mixture thereof.

The compounds of Formula II are useful as chemical intermediates for the synthesis of $^{11}$C-labeled compounds.

The invention also relates to methods for synthesizing a $^{11}$C-labeled compound, comprising allowing a compound of Formula II to react with [$^{11}$C]methyl iodide under conditions that are sufficient to synthesize a $^{11}$C-labeled compound.

The present invention may be understood more fully by reference to the following detailed description and illustrative examples, which are intended to exemplify non-limiting embodiments of the invention.

DETAILED DESCRIPTION OF THE INVENTION

The term "C$_1$-C$_6$ alkyl" as used herein refers to a straight or branched chain, saturated hydrocarbon having from 1 to 6 carbon atoms. Representative C$_1$-C$_6$ alkyl groups include, but are not limited to, methyl, ethyl, n-propyl, iso-propyl, n-butyl, iso-butyl, sec-butyl, tert-butyl, n-pentyl, iso-pentyl, neopentyl, n-hexyl, iso-hexyl, and neohexyl.

Examples of a mammal include, but are not limited to, a human, mouse, rat, guinea pig, horse, dog, cat, cow, pig, monkey, chimpanzee, and baboon.

The term "substantially free of its corresponding (S)-enantiomer" as used herein means that the $^{11}$C-labeled compound or compound of Formula II contains no more than about 10% by weight of its corresponding (S)-enantiomer, in another embodiment, no more than about 5% by weight of its corresponding (S)-enantiomer, in another embodiment no more than about 1% by weight of its corresponding (S)-enantiomer, in another embodiment no more than about 0.5% by weight of its corresponding (S)-enantiomer, and in another embodiment no more than about 0.1% by weight of its corresponding (S)-enantiomer.

The term "substantially free of its corresponding (R)-enantiomer" as used herein means that the $^{11}$C-labeled compound or compound of Formula II contains no more than about 10% by weight of its corresponding (R)-enantiomer, in another embodiment, no more than about 5% by weight of its corresponding (R)-enantiomer, in another embodiment no more than about 1% by weight of its corresponding (R)-enantiomer, in another embodiment no more than about 0.5% by weight of its corresponding (R)-enantiomer, and in another embodiment no more than about 0.1% by weight of its corresponding (R)-enantiomer.

Examples of a pharmaceutically acceptable salt include, but are not limited to, a hydrochloride, a hydrobromide, a hydroiodide, a nitrate, a sulfate, a bisulfate, a phosphate, an acid phosphate, an isonicotinate, an acetate, a lactate, a salicylate, a citrate, an acid citrate, a tartrate, a pantothenate, a bitartrate, an ascorbate, a succinate, a maleate, a fumarate, a gluconate, a glucaronate, a saccharate, a formate, a benzoate, a glutamate, a methanesulfonate, an ethanesulfonate, a benzenesulfonate, and a p-toluenesulfonate salt.

As used herein, the term "effective amount" refers to an amount of a $^{11}$C-labeled compound of Formula I that is effective for imaging tissue or labeling tissue in a mammal.

The invention provides $^{11}$C-labeled compounds of Formula I:

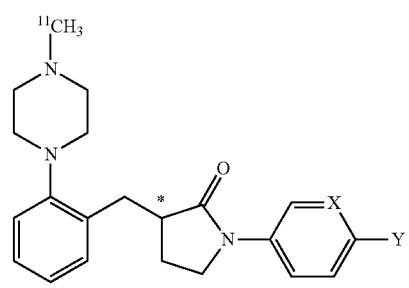

Formula I wherein X is CH or N;
Y is —C(OR$^1$)(R$^2$)$_2$ or —N(R$^3$)$_2$;
R$^1$ is H or C$_1$-C$_6$ alkyl;
each R$^2$ is independently C$_1$-C$_6$ alkyl, or both R$^2$ groups are taken together form —(CH$_2$)$_n$—, where n is an integer ranging from 2 to 7;
each R$^3$ is independently C$_1$-C$_6$ alkyl, or both R$^3$ groups are taken together to form —(CH$_2$)$_2$—O—(CH$_2$)$_2$—, —(CH$_2$)$_2$—(NR$^4$)—(CH$_2$)$_2$— or —(CH$_2$)$_m$—, where m is an integer ranging from 2 to 7;
R$^4$ is H or CH$_3$; and
* is a chiral carbon atom, wherein said carbon is a racemate, an (R)-enantiomer, an (S)-enantiomer, or a mixture thereof.

The present invention also provides compositions comprising an effective amount of a $^{11}$C-labeled compound and a physiologically acceptable carrier or vehicle.

The present invention also provides methods or uses for quantitatively imaging tissue, comprising administering an effective amount of a $^{11}$C-labeled compound to a mammal and detecting binding of the $^{11}$C-labeled compound in the mammal. This includes quantitatively imaging tissue that contains the 5HT$_{1B}$ receptor.

The present invention also provides methods or uses for labeling tissue, comprising administering an effective amount of a $^{11}$C-labeled compound to a mammal. This includes labeling tissue that contains the 5HT$_{1B}$ receptor.

In one embodiment, X is CH. In another embodiment, X is N.

In one embodiment, Y is —C(OR$^1$)(R$^2$)$_2$. In another embodiment, Y is —N(R$^3$)$_2$.

In one embodiment, $R^1$ and each $R^2$ group are —$CH_3$. In another embodiment, $R^1$ is H and each $R^2$ group is —$CH_2CH_3$. In another embodiment, $R^1$ is H and both $R^2$ groups are taken together to form —$(CH_2)_4$—.

In another embodiment, both $R^3$ groups are taken together to form —$(CH_2)_2$—O—$(CH_2)_2$—.

In one embodiment, X is CH, Y is —$C(OR^1)(R^2)_2$ and $R^1$ and each $R^2$ group are —$CH_3$.

It is understood that each variable of Formula I may have any definition described herein.

Formula I depicts an (*)-denoted carbon atom, which is chiral. With respect to the (*)-denoted carbon atom, Formula I encompasses a racemate, an (R)-enantiomer, an (S)-enantiomer, or a mixture thereof.

In one embodiment, the $^{11}C$-labeled compound is racemic with respect to the (*)-denoted carbon atom.

A $^{11}C$-labeled compound that is racemic with respect to the (*)-denoted carbon atom has the formula:

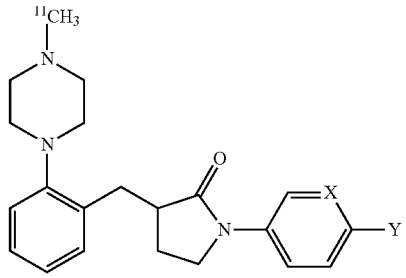

where X and Y are as defined above.

In another embodiment, a $^{11}C$-labeled compound is an (R)-enantiomer with respect to the (*)-denoted carbon atom and is substantially free of its corresponding (S)-enantiomer with respect to the (*)-denoted carbon atom.

A $^{11}C$-labeled compound that is an (R)-enantiomer with respect to the (*)-denoted carbon atom and that is substantially free of its corresponding (S)-enantiomer with respect to the (*)-denoted carbon atom has the formula:

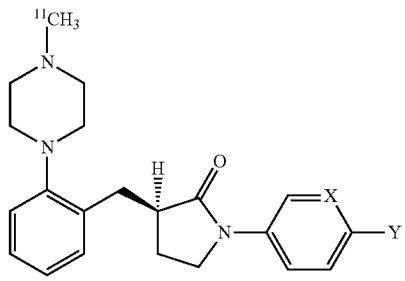

where X and Y are defined above.

In another embodiment, a $^{11}C$-labeled compound is an (S)-enantiomer with respect to the (*)-denoted carbon atom and is substantially free of its corresponding (R)-enantiomer with respect to the (*)-denoted carbon atom.

A $^{11}C$-labeled compound that is an (S)-enantiomer with respect to the (*)-denoted carbon atom and that is substantially free of its corresponding (R)-enantiomer with respect to the (*)-denoted carbon atom has the formula:

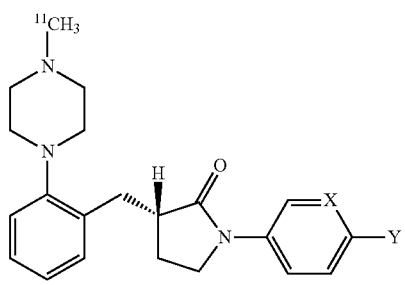

where X and Y are defined above.

In one embodiment, the $^{11}C$-labeled compound is independently any one or more of the following:

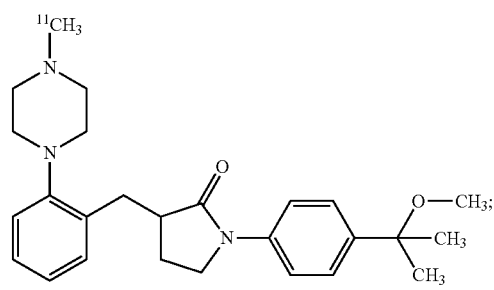
(compound I-A)

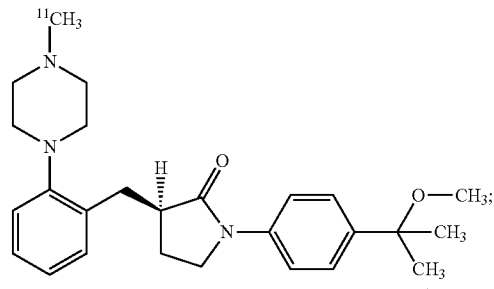
(compound I-B)

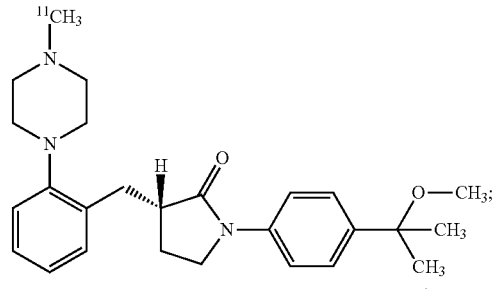
(compound I-C)

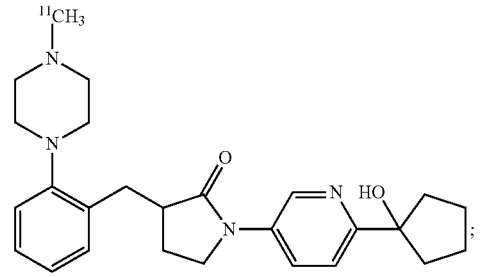
(compound I-D)

(compound I-E)
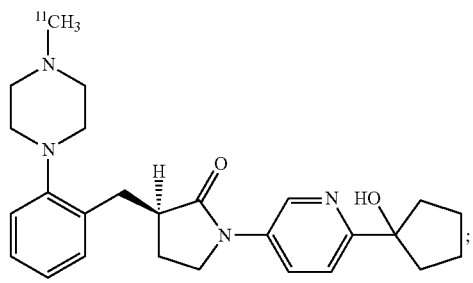

(compound I-F)
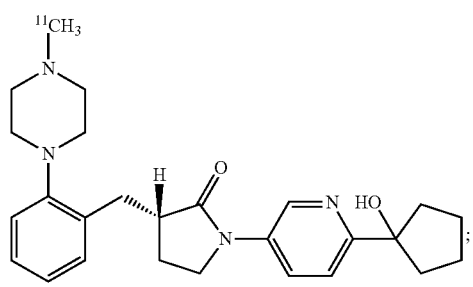

(compound I-G)
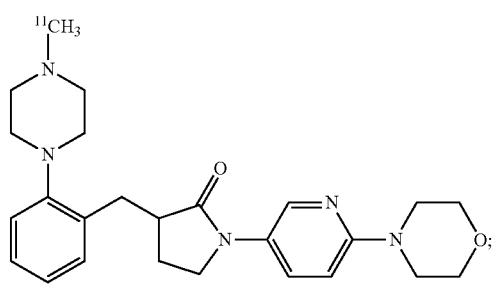

(compound I-H)
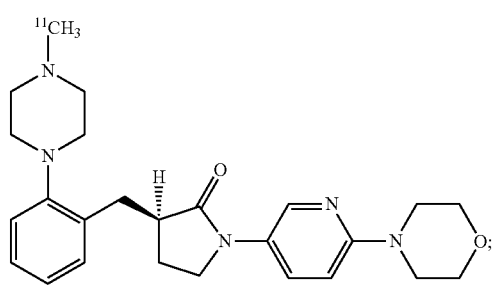

(compound I-J)
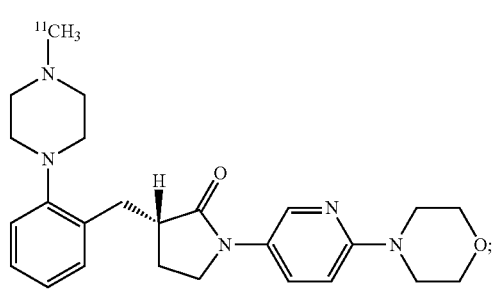

(compound I-K)
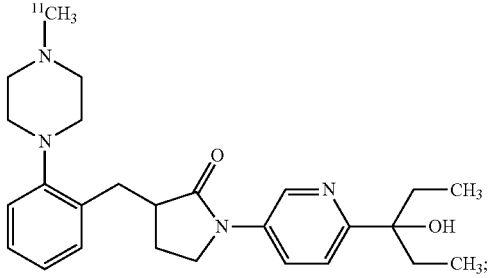

(compound I-L)
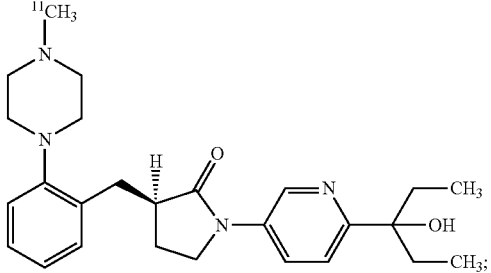

(compound I-M)
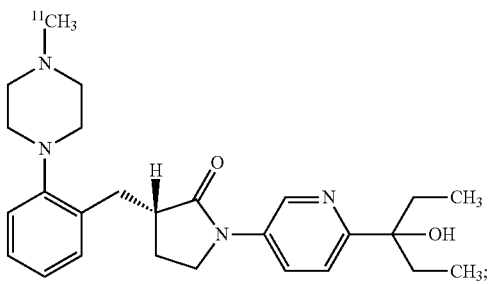

or, a pharmaceutically acceptable salt thereof.

In one embodiment, the $^{11}$C-labeled compound binds to a serotonin receptor. In another embodiment, the $^{11}$C-labeled compound binds to a 5HT$_{1B}$ receptor. In another embodiment, the $^{11}$C-labeled compound is a 5HT$_{1B}$-receptor antagonist.

The invention also provides compounds of Formula II:

Formula II
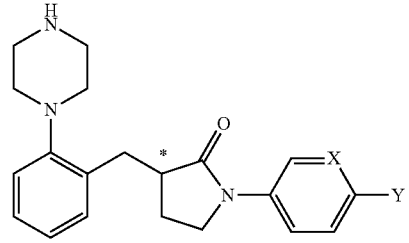

wherein X is CH or N;

Y is $-C(OR^1)(R^2)_2$ or $-N(R^3)_2$;

$R^1$ is H or $C_1$-$C_6$ alkyl;

each $R^2$ is independently $C_1$-$C_6$ alkyl, or both $R^2$ groups are taken together form $-(CH_2)_n-$, where n is an integer ranging from 2 to 7;

each $R^3$ is independently $C_1$-$C_6$ alkyl, or both $R^3$ groups are taken together to form —$(CH_2)_2$—O—$(CH_2)_2$—, —$(CH_2)_2$—$(NR^4)$—$(CH_2)_2$— or —$(CH_2)_m$—, where m is an integer ranging from 2 to 7;

$R^4$ is H or $CH_3$; and

* is a chiral carbon atom, wherein said carbon is a racemate, an (R)-enantiomer, an (S)-enantiomer, or a mixture thereof.

In one embodiment, X is CH. In another embodiment, X is N.

In one embodiment, Y is —$C(OR^1)(R^2)_2$. In another embodiment, Y is —$N(R^3)_2$.

In one embodiment, $R^1$ is H and each $R^2$ group is —$CH_2CH_3$. In another embodiment, $R^1$ is H and both $R^2$ groups are taken together to form —$(CH_2)_4$—.

In another embodiment, both $R^3$ groups are taken together to form —$(CH_2)_2$—O—$(CH_2)_2$—.

In one embodiment, X is CH, Y is —$C(OR^1)(R^2)_2$ and $R^1$ and each $R^2$ group are —$CH_3$.

It is understood that each variable of Formula II may have any definition described herein.

Formula II depicts an (*)-denoted carbon atom, which is chiral. With respect to the (*)-denoted carbon atom, Formula II encompasses a racemate, an (R)-enantiomer, an (S)-enantiomer, and a mixture thereof.

In one embodiment, a compound of Formula II is racemic with respect to the (*)-denoted carbon atom.

A compound of Formula II that is racemic with respect to the (*)-denoted carbon atom has the formula:

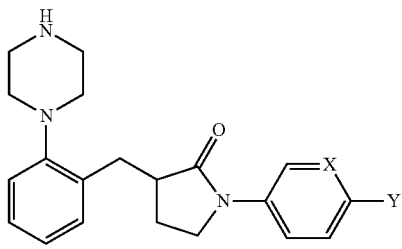

where X and Y are as defined above.

In another embodiment, a compound of Formula II is an (R)-enantiomer with respect to the (*)-denoted carbon atom and is substantially free of its corresponding (S)-enantiomer with respect to the (*)-denoted carbon atom.

A compound of Formula II that is an (R)-enantiomer with respect to the (*)-denoted carbon atom and that is substantially free of its corresponding (S)-enantiomer with respect to the (*)-denoted carbon atom has the formula:

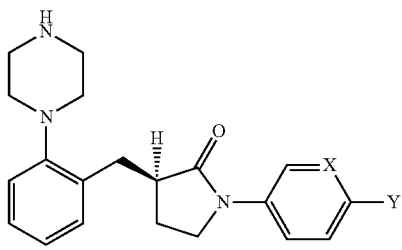

where X and Y are defined above.

In another embodiment, a compound of Formula II is an (S)-enantiomer with respect to the (*)-denoted carbon atom and is substantially free of its corresponding (R)-enantiomer with respect to the (*)-denoted carbon atom.

A compound of Formula II that is an (S)-enantiomer with respect to the (*)-denoted carbon atom and that is substantially free of its corresponding (R)-enantiomer with respect to the (*)-denoted carbon atom has the formula:

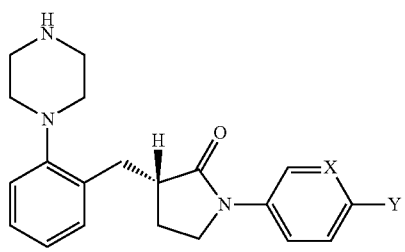

where X and Y are defined above.

In one embodiment, the compound of Formula II is independently any one or more of the following:

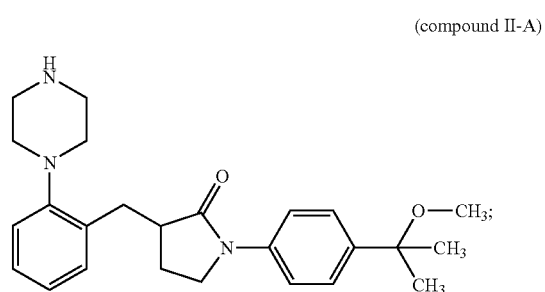

(compound II-A)

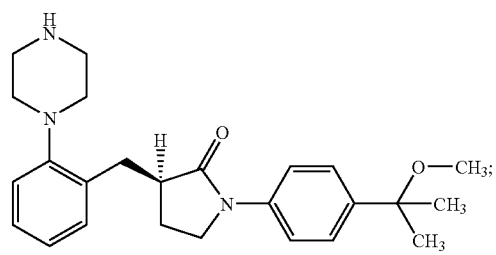

(compound II-B)

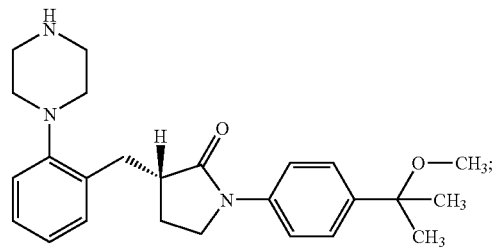

(compound II-C)

(compound II-D)
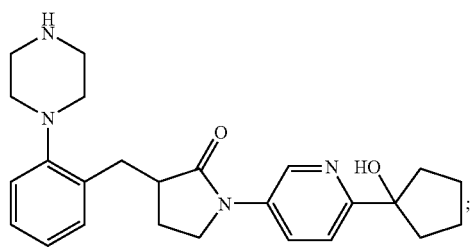
(compound II-E)
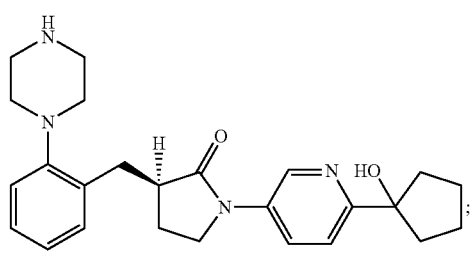
(compound II-F)
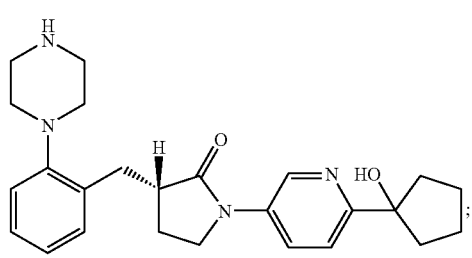
(compound II-G)
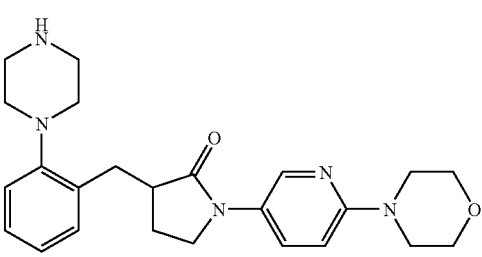
(compound II-H)
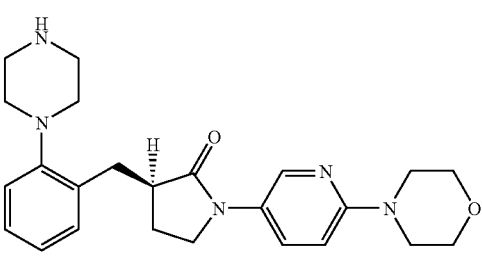
(compound II-J)
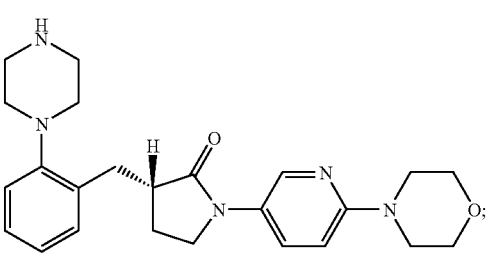
(compound II-K)
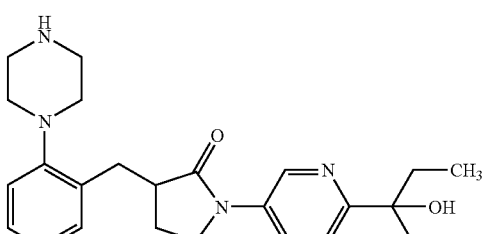
(compound II-L)
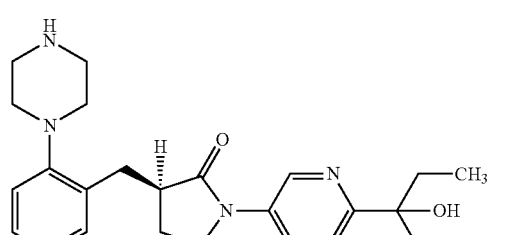
(compound II-M)
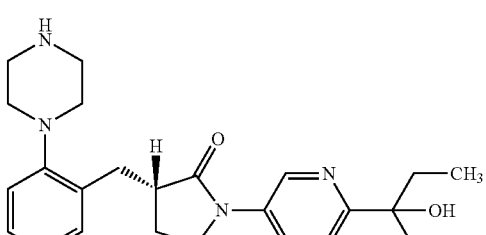
The compounds of Formula II and $^{11}$C-labeled compounds can be synthesized as shown generally in Schemes 1 and 2. Scheme 1 illustrates a synthesis of a pyrrolidin-2-one intermediate, 3-(2-piperazin-1-yl-benzyl)-pyrrolidin-2-one (6).
Scheme 1:
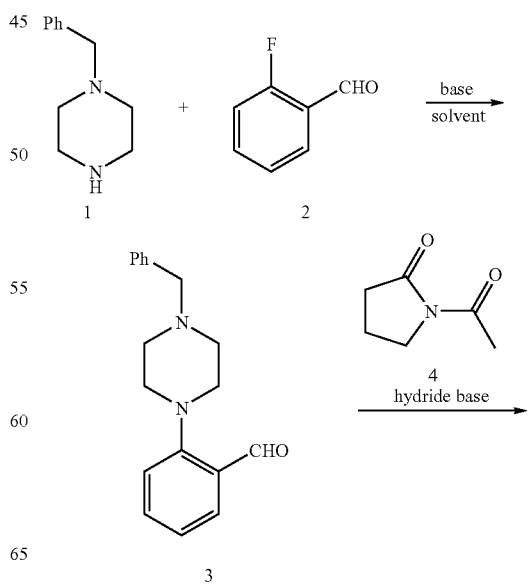

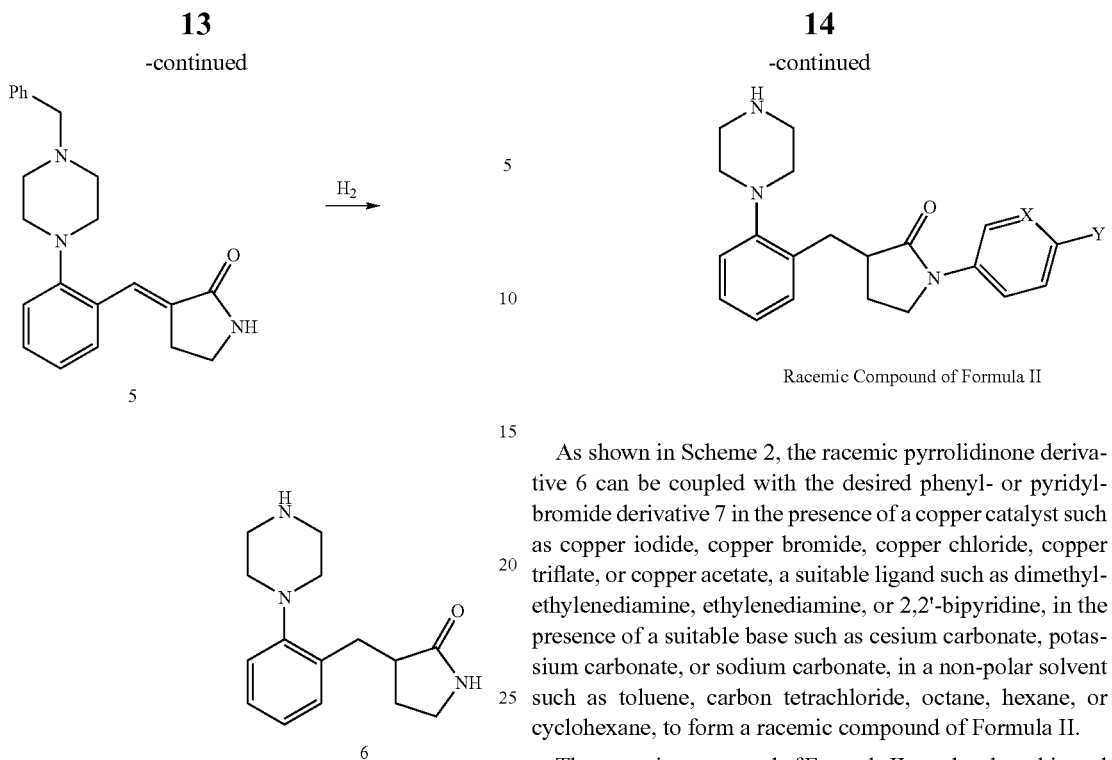

In Scheme 1, benzylpiperazine (1) and 2-fluorobenzaldehyde (2) are allowed to react in the presence of a suitable base, such as, for example, an alkali metal or alkaline earth base, including $K_2CO_3$ and $Na_2CO_3$, in the presence of a polar organic solvent, such as dioxane, water, acetone, tetrahydrofuran ("THF"), dimethylsulfoxide ("DMSO"), dimethylformamide ("DMF"), N-methylpyrrolidine ("NMP"), pyridine, dichloromethane, or a mixture thereof to provide the benzaldehyde derivative 3. Reaction of the benzaldehyde 3 in the presence of N-acetylpyrrolidinone (4) and hydride base such as sodium hydride, lithium aluminum hydride, or sodium aluminum hydride provides 5. Treatment of 5 with $H_2$ in the presence of palladium on carbon removes the benzyl protecting group and reduces the double bond of 5 to provide the racemic pyrrolidinone derivative 6. The skilled worker will understand that similar procedures would be efficacious in performing the aldol condensation wherein groups other than acyl are present on the pyrrolidinone ring, such as pivaloyl.

As shown in Scheme 2, the racemic pyrrolidinone derivative 6 can be coupled with the desired phenyl- or pyridyl-bromide derivative 7 in the presence of a copper catalyst such as copper iodide, copper bromide, copper chloride, copper triflate, or copper acetate, a suitable ligand such as dimethylethylenediamine, ethylenediamine, or 2,2'-bipyridine, in the presence of a suitable base such as cesium carbonate, potassium carbonate, or sodium carbonate, in a non-polar solvent such as toluene, carbon tetrachloride, octane, hexane, or cyclohexane, to form a racemic compound of Formula II.

The racemic compound of Formula II can then be subjected to chiral resolution to provide an (R)-enantiomer with respect to the (*)-denoted carbon atom of Formula II that is substantially free of its (S)-enantiomer with respect to the (*)-denoted carbon atom, or an (S)-enantiomer with respect to the (*)-denoted carbon atom of Formula II that is substantially free of its (R)-enantiomer with respect to the (*)-denoted carbon atom, using techniques known to those of skill in the art. For example, the racemic compound of Formula II can be subjected to chiral liquid chromatography ("LC") using a preparatory column appropriate for separating racemic compounds, including, for example, CHIRALCEL OD-H column, CHIRALPAK AD-H column, CHIRALPAK AS-H column, and CHIRALCEL OJ-H column, available commercially from Chiral Technologies, Inc., using solvent systems such as, for example, 0 to 40% methanol or ethanol in heptane, hexane, or acetonitrile ("ACN"); optionally including less than about 0.5% trifluoroacetic acid or less than about 0.5% diethylamine or triethylamine.

Scheme 2:

Scheme 3:

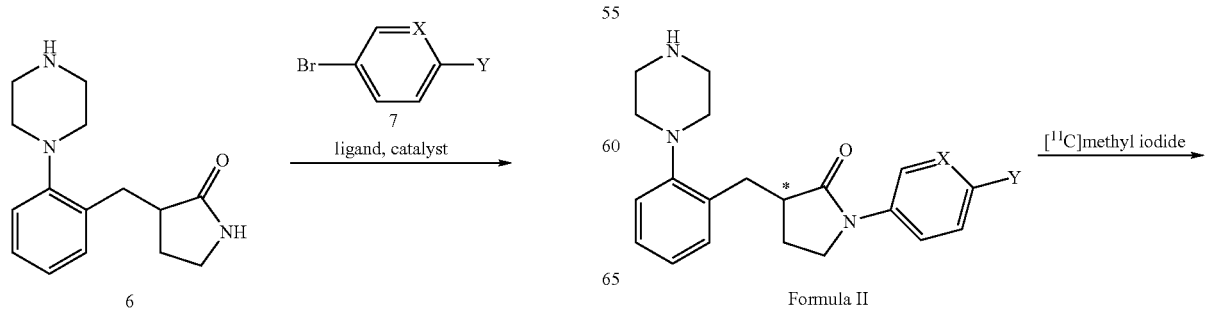

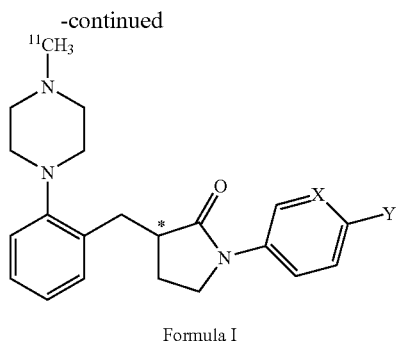

Formula I

As shown in Scheme 3, compounds of Formula II are N-methylated with [$^{11}$C]methyl iodide to provide the $^{11}$C-labeled compounds of the present invention. N-methylation can occur in a suitable polar aprotic solvent such as DMF, DMSO, ACN, or acetone. Methods for generating [$^{11}$C]methyl iodide are known to those of ordinary skill in the art. One example is disclosed in Långström B. and Lundqvist H., *Int. J. Appl. Radiat. Isot.*, 1976, 27, 357-363.

The present invention also provides compositions comprising an effective amount of a compound of Formula I and a physiologically acceptable carrier or vehicle. The compounds of Formula I may be administered by any means that achieve their intended purpose. For example, administration may be by parenteral, including subcutaneous, intravenous, intramuscular, intraperitoneal, transdermal, or buccal, routes. Alternatively, or concurrently, oral administration may be employed. A preferred route of administration of the compounds of Formula I for imaging is the intravenous route. The compounds of Formula I can be administered in a single bolus, or by gradual perfusion, which is preferably intravenous, using peristaltic means to accomplish the gradual perfusion.

The compounds of Formula I may be formulated in biocompatible solubilizing media for enteral or parenteral administration. The PET formulations of the invention may contain conventional pharmaceutical carriers and excipients appropriate for the type of administration contemplated. Formulations for enteral administration may vary widely, as is well-known in the art. In general, such formulations include a diagnostically effective amount of a ligand of the invention (compounds of Formula I) in an aqueous solution or suspension. Such enteral compositions may optionally include buffers, surfactants, adjuvants, thixotropic agents, and the like. Parenteral formulations advantageously contain a sterile aqueous or non-aqueous solution or suspension or emulsion of a ligand according to this invention. Various techniques for preparing suitable pharmaceutical solutions and suspensions are known in the art. Such solutions also may contain pharmaceutically acceptable buffers, stabilizers, antioxidants, and electrolytes, such as sodium chloride. Parenteral compositions may be injected directly or mixed with a large volume parenteral composition for systemic administration. Examples of non-aqueous solvents are propyleneglycol, polyethyleneglycol, vegetable oil, such as olive oil, and injectable organic esters, such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also present, such as, for example, antimicrobials, anti-oxidants, chelating agents, and inert gases. See, generally, Remington's Pharmaceutical Science, 16th ed., 1980.

The labeled compositions within the scope of the present invention are administered in doses effective to achieve the desired PET image. Such doses may vary widely, depending upon the activity level of the C-11 generated, the organs or tissues which are the subject of the imaging procedure, the PET equipment being used, etc. Typical doses of the diagnostic compositions are in the range from about 4 to about 400 pmol/kg body weight, and preferably about 200 pmol/kg body weight.

The invention is also useful as a means to evaluate the efficacy of, and responses to, therapeutic treatment of various CNS disorders such as depression and anxiety. In such a utility, the compounds of Formula I are used in a conventional manner in PET imaging procedures.

In one embodiment, the dose of a $^{11}$C-labeled compound is an amount that has sufficient radioactivity to enable labeling or imaging of tissue or an organ's expression of the receptor system using a technique such as PET. A dose useful for labeling or imaging a tissue typically ranges from about 1 MBq/kg to about 20 MBq/kg, but can vary according to factors such as the general health, age, and sex of the mammal and the particular application.

In one embodiment, the present methods further comprise administering an effective amount of a serotonin reuptake inhibitor ("SRI") (e.g., sertraline, fluoxetine, fenfluramine, or fluvoxamine) to the mammal. In this embodiment, the $^{11}$C-labeled compound and the SRI can be administered within the same composition, or separately. Where the $^{11}$C-labeled compound and SRI are administered separately, the administration is such that the SRI is inhibiting the reuptake of serotonin during a time where the $^{11}$C-labeled compound is labeling tissue in a mammal.

An effective dose of the SRI is generally within the range of about 1 mg to about 400 mg/mammal/day.

In one embodiment, the present methods further comprise administering an effective amount of a serotonin-2 ("5HT$_2$") receptor antagonist (e.g., ketanserin, pelanserin, pipamperone, spiperone, pirenperin or ritanserin) to the mammal. In this embodiment, the $^{11}$C-labeled compound and the 5HT$_2$ receptor antagonist can be administered within the same composition, or separately. Where the $^{11}$C-labeled compound and 5HT$_2$ receptor antagonist are administered separately, administration is such that the 5HT$_2$ receptor antagonist is inhibiting the 5HT$_2$ receptor during a time where the $^{11}$C-labeled compound is labeling a tissue in a mammal.

An effective amount of the 5HT$_2$ antagonist is generally within the range of about 1 mg to about 400 mg/mammal/day.

In one embodiment, the present methods further comprise administering an effective amount of a serotonin-1 ("5HT$_1$") receptor antagonist (e.g., a 5HT$_{1B}$ antagonist) to the mammal. In this embodiment, the $^{11}$C-labeled compound and the 5HT$_{1B}$ receptor antagonist can be administered within the same composition, or separately. Where the $^{11}$C-labeled compound and 5HT$_{1B}$ receptor antagonist are administered separately, administration is such that the 5HT$_{1B}$ receptor antagonist is inhibiting the 5HT$_{1B}$ receptor during a time where the $^{11}$C-labeled compound is labeling a tissue in a mammal.

An effective amount of the 5HT$_{1B}$ antagonist is generally within the range of about 1 mg to about 400 mg/mammal/day.

The invention also encompasses methods for imaging tissue, comprising administering an effective amount of a $^{11}$C-labeled compound to a mammal and detecting binding of the $^{11}$C-labeled compound in the mammal.

In one embodiment, detecting binding comprises detecting a radioactive emission from the $^{11}$C-labeled compound. The tissue can be epithelial tissue, connective tissue, muscle tissue, or nerve tissue. In one embodiment, the tissue is an organ.

Representative tissue includes brain, spinal cord, nerve, heart, blood vessel, blood, mouth, esophagus, stomach, small intestine, large intestine, colon, liver, lung, skin, eye, nose, trachea, kidney, bladder, urethra, ovary, uterus, vagina, breast, or testicle. In one embodiment, the tissue is brain. In another embodiment, the brain is globus pallidus, ventral pallidum, lentiform nucleus, striatum, substantia nigra, frontal lobe, temporal lobe, occipital cortex, cerebrum, or cerebellum.

In one embodiment, the tissue expresses serotonin receptors. In another embodiment, the tissue expresses $5HT_{1B}$ receptors. There are specifically high levels of $5HT_{1B}$ expression in the globus pallidus and substantia nigra, but significant expression is observed in all brain grey matter except cerebellar grey matter.

In one embodiment, the mammal is a human.

Imaging can be carried out using any appropriate apparatus. Imaging can be carried out on a conscious or unconscious mammal using standard imaging techniques in order to evaluate, for example, blood flow, pharmacokinetic parameters, and pharmacodynamic parameters before and after administration of a $^{11}$C-labeled compound. Physiological parameters that can be evaluated include, for example, $F_v$ (vascular fraction), $K_1$, $k_2$ (plasma/free compartment exchange rate), $k_{off}$, $k_{on}/V_r$ (association and dissociation rate), $B_{max}$ (receptor concentration), and $K_d$ (apparent equilibrium dissociation rate) of a $^{11}$C-labeled compound. Imaging can also be used to examine metabolic routes of a $^{11}$C-labeled compound.

Methods for PET imaging are described in, for example, C. Halldin et al., *Curr. Pharm. Design*, 2001, 7(18) 1907-29; C.-Y. Shiue et al., *Synapse*, 1997, 25, 147; and S. Houle et al., *Can. Nucl. Med. Commun.*, 1997, 18, 1130.

Therefore, the following examples further describe and demonstrate certain embodiments within the scope of the present invention. The examples are given solely for the purpose of illustration, and are not to be construed as limitations of the present invention since many variations of the present invention are possible without departing from its spirit and scope.

EXAMPLES

Example 1

Synthesis of 1-acetyl-pyrrolidin-2-one

A mixture of 112 g of 2-pyrrolidinone (9) and 249 mL of acetic anhydride was heated at reflux for 2 hours. The resultant mixture was allowed to cool to room temperature, was concentrated in vacuo, and was distilled (0.8 mm Hg, 68° C.) to provide 160 g of N-acetyl-2-pyrrolidinone (4) in 96% yield.

Example 2

Synthesis of 1-bromo-4-(1-methoxy-1-methyl-ethyl)-benzene

A mixture of 6.87 g of ethyl 4-bromobenzoate (10) was allowed to react with 64 mL (1.4 M in toluene) of methyl magnesium bromide in THF at −40° C. for 1 hour, and the reaction mixture was gradually warmed to 0° C. The reaction was quenched with saturated aqueous ammonium chloride solution and the resultant mixture was extracted with ethyl acetate. The organic layer was washed with brine, was dried over magnesium sulfate, was filtered, and the solvent was removed in vacuo. Purification by silica gel chromatography (50:1 to 10:1 hexanes-ethyl acetate) afforded 6.44 g (99% yield) of 2-(4-bromophenyl)propan-2-ol; MS (AP/CI) observed: 199.1 (M+H–$H_2O$)$^+$, 100%; 213.1, 215.1 (M–H)$^−$, 60%, 80%. 2-(4-Bromophenyl)propan-2-ol (1.77 g) and iodomethane (1.16 g) in THF (100 mL) were treated with sodium hydride, 60% in mineral oil (328 mg). After stirring for 24 h at room temperature, the reaction mixture was quenched with dilute aqueous hydrochloric acid, was extracted with ethyl acetate, and the organic layer was washed with brine, was dried over magnesium sulfate, was filtered, and the solvent was removed in vacuo. The resultant oil was purified by silica gel chromatography (200:1 hexanes-ethylacetate) to afford 0.5 g of 1-bromo-4-(1-methoxy-1-methyl-ethyl)-benzene; $^{13}$C NMR (400 MHz, CDCl$_3$) δ 145.35, 131.53, 127.91, 121.00, 50.90, 28.60.

Example 3

Synthesis of 1-[4-(1-methoxy-1-methyl-ethyl)-phenyl]-3-(2-piperazin-1-yl-benzyl)-pyrrolidin-2-one (compound 12)

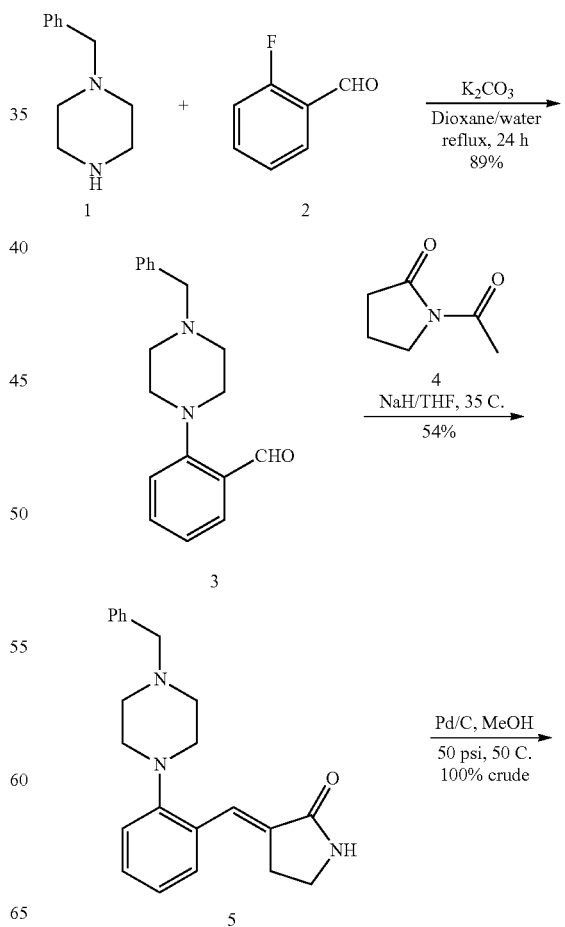

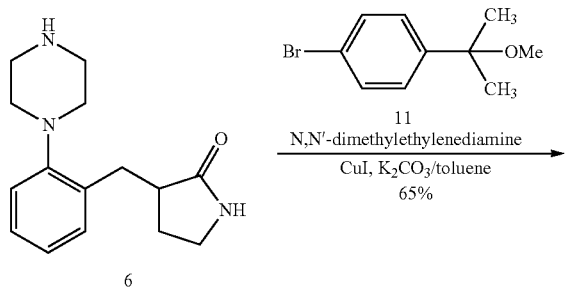

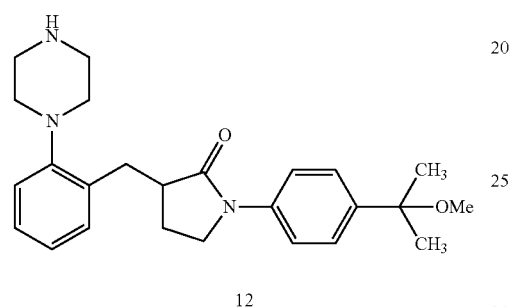

A mixture of 25 g of benzylpiperazine (1) and 10 g of 2-fluorobenzaldehyde (2) were allowed to react in refluxing dioxane/water (1:2, 90 mL total volume) for 24 hours in the presence of 17 g $K_2CO_3$. The resultant reaction mixture was allowed to cool to room temperature, was extracted with methylene chloride and the organic layer was then washed with water, 5% hydrochloric acid, brine, and was then dried over magnesium sulfate, was filtered, and the solvent was removed in vacuo. Purification by silica gel chromatography (5:1 hexanes-ethyl acetate) afforded 20 g of the benzaldehyde 3 in 89% yield; MS (AP/CI) observed: 281.1 (M+H)+ (100%). The benzaldehyde 3 (8 g) was subsequently allowed to react with 7.3 g of 1-acetyl-pyrrolidin-2-one (4) in the presence of 4.6 g of NaH (60% in mineral oil) at 0° C. for 1 hour followed by warming to room temperature and stirring for 2 hours. After quenching carefully with methanol at 0° C., the solvent was removed in vacuo, the residue was diluted with water, was extracted with methylene chloride and the organic extracts were washed with brine and were dried over magnesium sulfate and were filtered. The solvent was removed in vacuo and the residue was purified by silica gel chromatography (40:1 chloroform-methanol) to provide 7.9 g of 3-[2-(4-benzyl -piperazin-1-yl)-benzylidene]-pyrrolidin-2-one (5) in 80% yield; MS (AP/CI) observed: 348.1 (M+H)+, 100%. Hydrogenation of 6.3 g of 5 with 1.5 g of Pd/C in 100 mL of methanol under 50 p.s.i. of pressure at 60° C. provided 3.8 g (82% yield) of 3-(2-piperazin-1-yl-benzyl)-pyrrolidin-2-one (6) following filtration, removal of solvent in vacuo, and purification by silica gel chromatography (30:1:0.3 chloroform-methanol-ammonium hydroxide); MS (AP/CI) observed: 260.1 (M+H)+, 100%.

3-(2-piperazin-1-yl-benzyl)-pyrrolidin-2-one (6) (1.2 grams) was subsequently allowed to react with 1.27 g of 1-bromo-4-(1-methoxy-1-methyl-ethyl)-benzene (11) in the presence of 0.041 grams of N,N'-dimethylethylenediamine, 0.088 g of CuI and 0.96 grams of $K_2CO_3$ in toluene (6 mL) at 110° C. for 17 hours to provide 1.2 grams of the racemate 1-[4-(1-methoxy-1-methyl-ethyl)-phenyl]-3-(2-piperazin-1-yl-benzyl)-pyrrolidin-2-one (12) (64% yield) following silica gel chromatography (40:1:0.5 chloroform-methanol-ammonium hydroxide); MS (AP/CI) observed: 408.2 (M+H)+.

Example 4

Synthesis of R-1-[4-(1-methoxy-1-methyl-ethyl)-phenyl]-3-(2-piperazin-1-yl-benzyl)-pyrrolidin-2-one (compound 13)

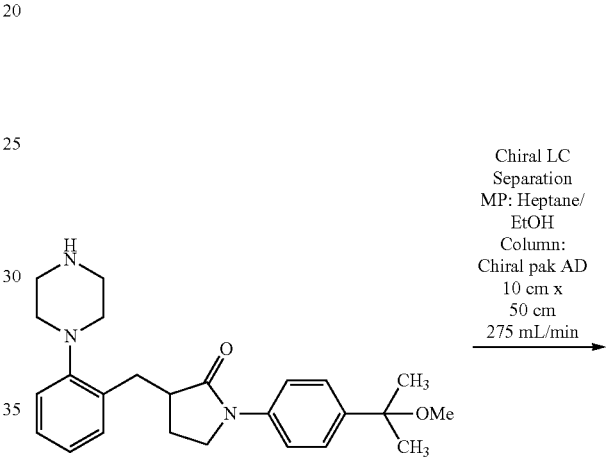

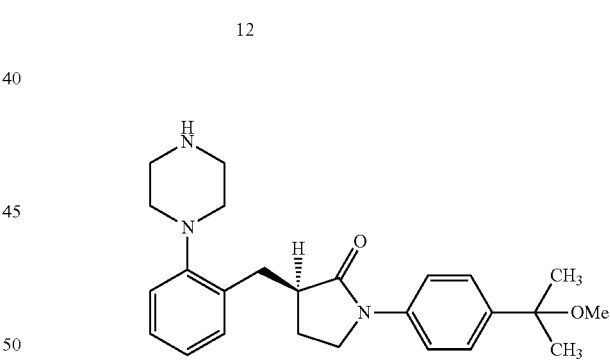

The racemic compound 12 (1137 milligrams) was subjected to chiral liquid chromatography separation using a CHIRALPAK AD 10×25 cm column, with a mobile phase of heptane/ethanol in a 75:25 ratio and a flow rate of 275 mL/min. Compound 13 exhibited a retention time of approximately 29 minutes and a UV max of 250 nM. The relevant fractions were collected and concentrated in vacuo to provide 0.488 grams of compound 13 (diagnostic $^{13}C$ NMR (400 MHz, $CDCl_3$) δ 175.93, 152.53, 142.09, 138.54, 135.30, 130.56, 127.63, 126.55, 124.54, 120.86, 119.62, 76.72, 54.16, 50.85, 46.98, 46.77, 44.99, 32.49, 28.17, 28.13, 24.69), which contained no more than about 0.5% by weight of its corresponding (S)-enantiomer.

Example 5

Synthesis of S-1-[4-(1-methoxy-1-methyl-ethyl)-phenyl]-3-(2-piperazin-1-yl-benzyl)-pyrrolidin-2-one (compound 14)

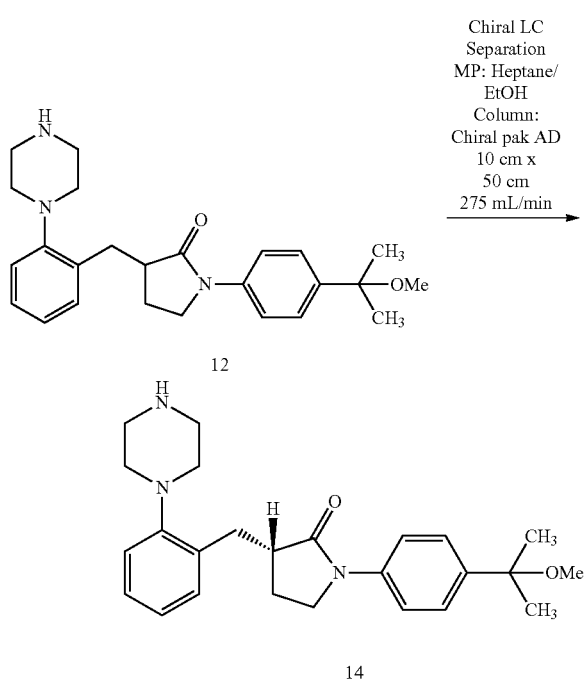

The racemic compound 12 (1137 milligrams) was subjected to chiral liquid chromatography separation using a CHIRALPAK AD 10×25 cm column, with a mobile phase of heptane/ethanol in a 75:25 ratio and a flow rate of 275 mL/min. Compound 14 exhibited a retention time of approximately 48 minutes and a UV max of 250 nM. The relevant fractions were collected and concentrated in vacuo to provide 0.70 grams of compound 14 (diagnostic $^{13}$C NMR (400 MHz, CDCl$_3$) δ 175.93, 152.54, 142.10, 138.54, 135.30, 130.56, 127.62, 126.55, 124.53, 120.86, 119.62, 76.72, 54.19, 50.84, 46.98, 46.80, 44.99, 32.48, 28.17, 28.13, 24.67), which contained no more than about 4% by weight of its corresponding (R)-enantiomer.

Example 6

Synthesis of R-1-[4-(2-methoxy-isopropyl)-phenyl]-3-[2-(4-[$^{11}$C]methyl-piperazin-1-yl)benzyl]-pyrrolidin-2-one (compound I-B)

[$^{11}$C]Carbon dioxide was generated using a Scanditronix MC-17 cyclotron using an $^{14}$N(p,α)$^{11}$C reaction with 17 MeV protons in a gas target containing nitrogen (AGA, Nitrogen 6.0) and 0.1% oxygen (AGA, Oxygen 4.8). Schlyer, D. J. (2003). Production of Radionuclides in Accelerators. *Handbook of Radiopharmaceuticals. Radiochemistry & Applications*. M. J. Welch and C. S. Redvanly. Chichester, John Wiley & Sons, Ltd., 1-70.

Liquid chromatographic purification and analysis were performed using a Beckman 126 gradient pump and a Beckman 166 variable-wavelength UV detector in series with β$^+$-flow detector. The following mobile phases were used for semi-preparative LC: saline (9 mg/mL) and acetonitrile/H$_2$O (50:7); for analytical LC: 0.05 M ammonium formate, pH 3.5 and acetonitrile/H$_2$O (50:7). A Jones Chromatography Genesis C$_{18}$ column (250×4.6 mm, i.d.) was used for analytical liquid chromatography at a flow rate of 2 mL/min. For semi-preparative LC, a Jones Chromatography Genesis C$_{18}$ column (4 μm, 250×10 mm, i.d.) was used at a flow rate of 6 mL/min. Synthia, an automated synthesis system available from Uppsala Imanet, was used for LC injection and fraction collection. Data collection and LC control were performed using a Beckman System Gold chromatography software package.

Radioactivity was measured using a Veenstra Instrumenten by VDC-202 ion chamber.

Synthesis of [$^{11}$C]methyl iodide

The trapped [$^{11}$C]carbon dioxide was released by heating the trap to 50° C. Once released, the [$^{11}$C]carbon dioxide was carried in a stream of nitrogen gas via stainless steel lines to a hot-cell and trapped in a suitably designed reaction vessel containing lithium aluminium hydride (0.2M) in tetrahydrofuran (200 μL). After transfer of the [$^{11}$C]carbon dioxide, the THF was evaporated by heating it to about 120° C. in a stream of dry nitrogen gas. Hydroiodic acid (1.5 mL, 54%) was added, and the resultant [$^{11}$C]methyl iodide was transferred in a stream of nitrogen gas via a drying tower (SICAPENT) to the reaction vessel.

Synthesis of Compound I-B

The [$^{11}$C]methyl iodide obtained above was trapped at ambient temperature into a DMF (200 μL) and DMSO (100 μL) solution of compound 13 (1 mg) in a pear-shape stoppered vial, and the resultant reaction mixture was heated at about 130° C. for 5 min. The reaction mixture was allowed to cool to room temperature and diluted with saline/acetonitrile (300 μL) and injected into the semi-preparative HPLC column. Fractions were collected, transferred to a rotary-evaporator flask, and concentrated by heating at 95° C. under vacuum. A sterile phosphate buffer solution (pH 7, 2.4 mL) and ethanol (0.6 mL, 99.5%) was transferred to the flask and subsequently transferred to a sterile injection vial containing 0.1 M sterile phosphate buffer solution (3 mL) by helium gas using a 0.22 μm filter. Standard chemical characterization methods verified the structure of compound I-B. Compound I-B contains no more than about 1.5% of its corresponding (S)-enantiomer, compound I-C.

Example 7

Receptor-Binding Experiments with Compound I-B

Experiments performed with compound I-B, including in-vitro autoradiographies and ex-vivo experiments in Guinea pig, and in-vivo PET-experiments in Rhesus monkeys, indicate a specific uptake of compound I-B mainly in the external globus pallidus and ventral pallidum. This uptake is sensitive to blocking by other 5HT$_{1B}$ antagonists in a dose dependent manner.

Example 8

Administration of Compound I-B for Imaging Tissue

Compound I-B is a 5HT$_{1B}$ receptor antagonist having physiochemical properties that make it useful for labeling or imaging tissue in a mammal. Compound I-B is also useful for measuring $5HT_{1B}$ receptor occupancy.

Less than about 20 μg of compound I-B, which corresponds to approximately 250-500 MBq in 0.1 M phosphate buffer (pH 7.4) containing <8% ethanol, is administered intravenously.

Screening takes place over a two-day trial period. On day 1, a single intravenous dose of about 10 mL of the phosphate-buffered compound I-B is administered to the mammal over about 30 seconds, and is followed by performing PET for 90 minutes. Arterial plasma samples are continuously withdrawn for 7 minutes with an on-line radioactivity detector. Arterial blood sampling provides a plasma input function for calculating specific brain regional uptake of compound I-B. This is followed by the taking of discrete arterial blood samples at 2, 5, 10, 20, 40, 60 and 90 minutes, to determine levels of plasma $^{11}C$ due to compound I-B and its metabolites. Subject symptoms and adverse events are monitored. On day 2, subjects are assessed within 1-10 days to repeat the assessments outlined above in Day 1.

The projected blood volume to be collected is approximately 175 mL.

Arterial blood samples are continuously withdrawn for 7 minutes with an on-line radioactivity detector at a speed of 4 mL/min, and discrete samples of 7 mL each are taken at 2, 5, 10, 20, 40, 60 and 90 minutes following dosing. HPLC analysis of arterial blood samples to determine levels of $^{11}C$ due to parent tracer and its metabolites is also performed.

Subjects receive an intravenous injection of compound I-B in up to 10 mL 0.1 M phosphate buffer (pH 7.4) containing <8% ethanol over approximately 30 seconds at the onset of the PET scan with a duration of 90 minutes. During PET, arterial blood sampling is performed to provide a plasma input function for calculating specific brain regional uptake of compound I-B. Initially, whole blood $^{11}C$ radioactivity is continuously monitored for 7 minutes using an on-line radio-activity detector to obtain peak activity levels. Also, discrete arterial blood samples are taken at 2, 5, 10, 20, 40, 60, and 90 minutes to determine levels of plasma $^{11}C$ radioactivity due to the parent tracer and its metabolites.

Subjects are placed in the scanner with transaxial planes orientated parallel to the orbito-meatal line. Dynamic compound I-B PET data are acquired in 3D mode for all subjects using either of the two identical ECAT EXACT HR+ (Siemens/CTI) scanners, which have a 15.5 cm axial field of view and generates 63 transaxial planes. The tomographs have a reconstructed spatial resolution of about 5-6 mm after image reconstruction. A transmission scan, which corrects for attenuation of emitted radiation by skull and tissue, is acquired during 10 minutes using three retractable $^{68}Ge$ line sources. An emission scan is then started simultaneously with start of tracer injection, and data are acquired over 90 minutes (divided into 18 successive time frames). Dynamic images are reconstructed using a filtered back projection algorithm with a Hanning filter.

For the analysis of the images, initially an average over the sequence is made and images are co-aligned with the subjects MRI images acquired at screening. A set of volumes of interest ("VOIs") are created and placed bilaterally over the globus pallidus (part of lentiform nucleus, striatum), (medial) frontal, lateral temporal and occipital cortex and cerebellum (cortex) to sample tracer uptake in these regions.

Depending on the actual pattern of tracer distribution in the human brain additional regions are also included.

The VOIs are applied to the uptake data, and dynamic TACs are generated. Various modeling exercises are undertaken in the work of verifying a suitable modeling approach. A metabolite-corrected plasma input function is generated and used.

The defined VOIs are then used to generate TACs from the dynamic time series. Patlak and Logan linear graphical methods are used to quantify tracer uptake as an influx constant $K_i$ in areas of irreversible binding (striatum) and specific volumes of distribution ($V_d$) in areas of reversible binding (cortex, thalamus) during the time course of PET. Assuming the cerebellum demonstrates rapid uptake and then washout, suggesting an absence of specific binding, the cerebellar time activity curve is used as a reference tissue input function. Alternatively, a metabolite-corrected arterial plasma input function is employed. The slope ($K_i$) obtained for an irreversibly trapped tracer and the $V_d$ obtained for a reversibly binding agent are both proportional to the binding potential ($B_{max}/K_d$ in the absence of cold ligand) of the tracer. The influx constant, $K_i$, has units of $min^{-1}$.

The tracer uptake is described and presented as TAC data combined with blood and plasma data as well as metabolite data.

Descriptive statistics for pharmacodynamic variables such as counts per second and specific to non-specific uptake ratio are tabulated. Satisfactory tracer measures a count rate in the head (decayed to time of tracer injection) of not less than 50,000 counts per second. Satisfactory tracer also has specific to non-specific uptake ratio greater than 0.5.

Plasma levels of $^{11}C$ due to compound I-B and its metabolites at 2 (only total $^{11}C$ measured), 5 (only total $^{11}C$ measured), 10, 20, 40, 60 and 90 minutes are determined.

Compound I-B can also be employed to measure the degree of brain $5HT_{1B}$ receptor occupancy of $5HT_{1B}$ receptor antagonists in development, which assists in the determination of efficacious dose. Gefvert O, et al. *Eur Neuropsychopharmacol.*, 2001, 11, 105-110; Bergström M, et al., *Biological Psychiatry*, 2004, 55, 1007-1012.

Throughout this application, various publications are referenced. The disclosures of these publications in their entireties are hereby incorporated by reference into this application.

What is claimed:
1. A compound of formula I:

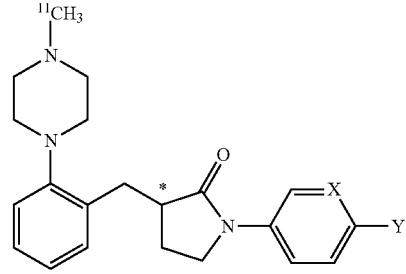

Formula I or a pharmaceutically acceptable salt thereof,
wherein
X is CH or N;
Y is —C(OR$^1$)(R$^2$)$_2$ or —N(R$^3$)$_2$;
R$^1$ is H or $C_1$-$C_6$ alkyl;
each R$^2$ is independently $C_1$-$C_6$ alkyl, or both R$^2$ groups are taken together form —(CH$_2$)$_n$—, where n is an integer ranging from 2 to 7;
each R$^3$ is independently $C_1$-$C_6$ alkyl, or both R$^3$ groups are taken together to form —(CH$_2$)$_2$—O—(CH$_2$)$_2$—, —(CH$_2$)$_2$—(NR$^4$)—(CH$_2$)$_2$— or —(CH$_2$)$_m$—, where m is an integer ranging from 2 to 7;
R$^4$ is H or CH$_3$; and
* is a chiral carbon atom, wherein the carbon is a racemate, an (R)-enantiomer, an (S)-enantiomer, or a mixture thereof.

2. The compound or pharmaceutically acceptable salt of the compound of claim 1, being racemic with respect to the (*)-denoted carbon atom; the compound or a pharmaceutically acceptable salt of the compound being an (R)-enantiomer with respect to the (*)-denoted carbon atom and being substantially free of its corresponding (S)-enantiomer with respect to the (*)-denoted carbon atom; or, the compound or a pharmaceutically acceptable salt of the compound being an (S)-enantiomer with respect to (*)-denoted carbon atom and being substantially free of its corresponding (R)-enantiomer with respect to the (*)-denoted carbon atom.

3. The compound or pharmaceutically acceptable salt of the compound of claim 2, wherein X is CH or N; Y is —C(OR$^1$)(R$^2$)$_2$ or —N(R$^3$)$_2$; and, R$^1$ and each R$^2$ group are —CH$_3$ or —CH$_2$CH$_3$.

4. The compound or pharmaceutically acceptable salt of the compound of claim 1, said compound having the structure:

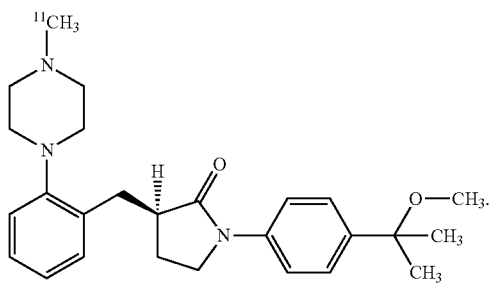

5. A composition comprising an effective amount of a compound or the pharmaceutically acceptable salt of the compound of claim 1 and a physiologically acceptable carrier or vehicle.

6. A method for imaging tissue, comprising:
   administering an effective amount of the compound or a pharmaceutically acceptable salt of claim 1 to a mammal; and
   detecting binding of the compound or pharmaceutically acceptable salt of the compound in the mammal.

7. The method of claim 6, wherein detecting binding comprises detecting a radioactive emission from the compound or pharmaceutically acceptable salt of the compound.

8. The method of claim 6, wherein the imaging comprises performing positron emission tomography.

9. The method of claim 6, wherein the tissue is a brain.

10. The method of claim 9, wherein the brain is globus pallidus and substantia nigra.

11. The method of claim 9, wherein the brain expresses 5HT$_{1B}$ receptors.

12. The method of claim 6, wherein the mammal is a human.

13. A method for labeling tissue, comprising:
   administering an effective amount of the compound or a pharmaceutically acceptable salt of claim 1 to a mammal.

14. A preparation for synthesizing a compound of Formula I of claim 1, comprising:
   reacting a compound of the Formula II:

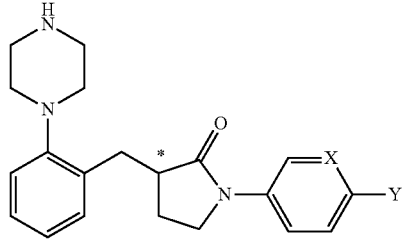

Formula II wherein X is CH or N;
Y is —C(OR$^1$)(R$^2$)$_2$ or —N(R$^3$)$_2$;
R$^1$ is H or C$_1$-C$_6$ alkyl;
each R$^2$ is independently C$_1$-C$_6$ alkyl, or both R$^2$ groups are taken together form —(CH$_2$)$_n$—, where n is an integer ranging from 2 to 7;
each R$^3$ is independently C$_1$-C$_6$ alkyl, or both R$^3$ groups are taken together to form —(CH$_2$)$_2$—O—(CH$_2$)$_2$—, —(CH$_2$)$_2$—(NR$^4$)—(CH$_2$)$_2$— or —(CH$_2$)$_m$— where m is an integer ranging from 2 to 7;
R$^4$ is H or CH$_3$; and
* is a chiral carbon atom, wherein the carbon is a racemate, an (R)-enantiomer, an (S)-enantiomer, or a mixture thereof;
with [$^{11}$C]methyl iodide under conditions that are sufficient to synthesize the compound of Formula I.

15. The preparation of claim 14, wherein the compound is

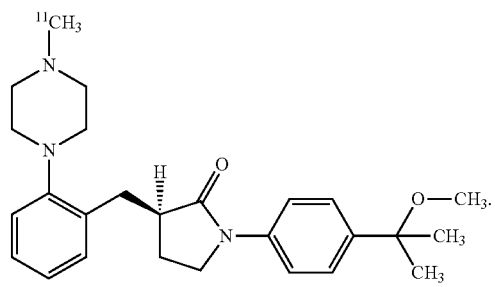

* * * * *